United States Patent
Ben-Haim

[11] Patent Number: 6,063,022
[45] Date of Patent: May 16, 2000

[54] CONFORMAL CATHETER

[75] Inventor: Shlomo Ben-Haim, Haifa, Israel

[73] Assignee: Biosense, Inc., New Brunswick, N.J.

[21] Appl. No.: 09/125,927

[22] PCT Filed: Dec. 31, 1997

[86] PCT No.: PCT/IL97/00448

§ 371 Date: Apr. 12, 1999

§ 102(e) Date: Apr. 12, 1999

[87] PCT Pub. No.: WO98/29032

PCT Pub. Date: Jul. 9, 1998

Related U.S. Application Data

[60] Provisional application No. 60/034,704, Jan. 3, 1997, and provisional application No. 60/034,703, Jan. 3, 1997.

[51] Int. Cl.[7] .................................................. A67B 17/38
[52] U.S. Cl. .......................................................... 600/41
[58] Field of Search ....................... 606/41, 49; 600/407, 600/509, 595

[56] References Cited

U.S. PATENT DOCUMENTS

| | | | |
|---|---|---|---|
| 4,570,354 | 2/1986 | Hindes | 33/534 |
| 4,651,436 | 3/1987 | Gaal | 33/533 |
| 4,921,482 | 5/1990 | Hammerslag et al. | 604/95 |
| 4,982,725 | 1/1991 | Hibino et al. | 128/4 |
| 5,042,486 | 8/1991 | Pfeiler et al. | 128/653 |
| 5,273,025 | 12/1993 | Sakiyama et al. | 128/6 |
| 5,295,484 | 3/1994 | Marcus et al. | 128/600.03 |
| 5,295,486 | 3/1994 | Wollschlager et al. | 128/661.01 |
| 5,316,024 | 5/1994 | Hirschi et al. | 128/899 |
| 5,391,199 | 2/1995 | Ben-Haim | 607/122 |
| 5,425,367 | 6/1995 | Shapiro et al. | 128/653.1 |
| 5,465,717 | 11/1995 | Imran et al. | 128/642 |
| 5,471,982 | 12/1995 | Edwards et al. | 128/642 |
| 5,558,073 | 9/1996 | Pomeranz et al. | 128/642 |
| 5,577,502 | 11/1996 | Darrow et al. | 128/653.1 |
| 5,617,857 | 4/1997 | Chader et al. | 128/653.1 |
| 5,671,739 | 9/1997 | Darrow et al. | 128/653.1 |
| 5,722,402 | 3/1998 | Swanson et al. | 606/41 |
| 5,730,129 | 3/1998 | Darrow et al. | 128/653.1 |
| 5,775,322 | 7/1998 | Silverstein et al. | 128/207.14 |
| 5,788,692 | 8/1998 | Campbell et al. | 606/41 |
| 5,868,673 | 2/1999 | Vesely | 600/407 |

FOREIGN PATENT DOCUMENTS

| | | |
|---|---|---|
| WO 92/03090 | 3/1992 | WIPO. |
| WO 94/00050 | 1/1994 | WIPO. |
| WO 95/04938 | 2/1995 | WIPO. |
| WO 95/19738 | 7/1995 | WIPO. |
| WO 96/05768 | 2/1996 | WIPO. |
| WO 97/24983 | 7/1997 | WIPO. |

*Primary Examiner*—William E. Kamm
*Attorney, Agent, or Firm*—Louis J. Capezzuto

[57] ABSTRACT

An invasive probe apparatus includes a flexible, elongate probe having a distal end for insertion into the patient's body, first and second position sensors in a fixed, known relation to the distal end for generating signals responsive to their respective position coordinates and at least one contact sensor along a radial surface of the probe for generating a signal representing its contact with body tissue to be ablated by electrodes on the probe.

10 Claims, 2 Drawing Sheets

6,063,022

CONFORMAL CATHETER

RELATED APPLICATIONS

This application claims the benefit of U.S. Provisional Patent Applications Ser. Nos. 60/034,703 and 60/034,704, filed Jan. 3, 1997, which are assigned to the assignee of the present patent application and incorporated herein by reference.

FIELD OF THE INVENTION

The present invention relates generally to cardiac diagnostic and therapeutic systems, and specifically to invasive medical probes that may be used to map the interior surfaces of the heart.

BACKGROUND OF THE INVENTION

Position-responsive cardiac catheters are known in the art. Such catheters are generally inserted percutaneously and fed through one or more major blood vessels into a chamber of the heart. A position-sensing device in the catheter, typically near the catheter's distal end, gives rise to signals that are used to determine the position of the device (and hence of the catheter) relative to a frame of reference that is fixed either externally to the body or to the heart itself. The position-sensing device may be active or passive and may operate by generating or receiving electrical, magnetic or ultrasonic energy fields or other suitable forms of energy known in the art.

U.S. Pat. No. 5,391,199, which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional position coordinates of the coil.

PCT patent publication number WO96/05768, filed Jan. 24, 1995, which is assigned to the assignee of the present application and whose disclosure is incorporated herein by reference, describes a position-responsive catheter comprising a plurality of miniature, preferably non-concentric sensor coils fixed in its distal end. As in the U.S. Pat. No. 5,391,199, electrical signals generated by these coils in response to an externally-applied magnetic field are analyzed so as to determine, in a preferred embodiment, six-dimensional position and orientation coordinates of the coils.

Multiple position-sensing devices may be placed in a known, mutually-fixed spatial relation at or adjacent to the distal end of a catheter, as described, for example, in PCT patent application no. PCT/IL97/00009, which is assigned to the assignee of the present application and whose disclosure is incorporated herein by reference. This application describes a catheter having a substantially rigid structure at its distal end, to which one or more position sensors are fixed. The sensors are used to determine the position and orientation of the structure, preferably for use in mapping electrical activity in the heart. Although the structure itself is substantially rigid, the remainder of the catheter is generally flexible, and the position sensors do not provide coordinate information regarding any points on the catheter proximal to the structure.

PCT publication WO95/04938, which is also incorporated herein by reference, describes a miniature magnetic field sensor coil and method of remotely determining the coil's location. The sensor coil may be used to determine the spatial configuration or course of flexible endoscope within the body of a subject in one of two ways: (1) By passing the coil through an internal lumen of the endoscope, for example, the endoscope's biopsy tube, and externally tracking the coil's location while the endoscope is held stationary; or (2) By distributing a plurality of the coils, preferably about a dozen, along the length of the endoscope and determining all of the coils' locations. The position coordinates determined with respect to each location of the coil (when a single coil is used) or to all the coils (when the plurality of coils are used) are taken together to interpolatively reconstruct the spatial configuration of the endoscope within the intestines of the subject, for example, and thereby estimate the corresponding spatial configuration of the intestines.

The accuracy of this endoscope in estimating the spatial configuration of the intestines depends on having a relatively large number of position measurements and/or of coils. Passing the coil (or other sensor element) through a lumen in the endoscope is time consuming and physically not practical for use in thin probes, such as cardiac catheters that must be passed through blood vessels. Using a large number of coils, however, undesirably increases the weight and cost of the catheter and reduces its flexibility.

U.S. Pat. No. 5,042,486, whose disclosure is further incorporated herein by reference, describes a method of locating a catheter within the body of a subject, generally within a blood vessel, by tracking the position of an electromagnetic or acoustic transmitter or receiver in the tip of the catheter. The position readings are registered with a previously acquired X-ray image of the blood vessel. This method is practical, however, only when the catheter is moving within a vessel or other physiological structure that defines a narrow channel within which the catheter's movement is constrained.

PCT publication WO 92/03090, whose disclosure is also incorporated herein by reference, describes a probe system, such as an endoscope, including sensing coils mounted at spaced positions along the probe. An array of antennas in a vicinity of the probe are driven by AC electrical signals, so as to induce corresponding voltage signals in the sensing coils. These signals are analyzed to determine three-dimensional coordinates of the coils. The locations of points along the probe, intermediate a pair of the sensing coils, may be determined by interpolation between the respective coordinates of the coils.

SUMMARY OF THE INVENTION

It is an object of the present invention to provide a flexible catheter, for insertion into a cavity in the body of a subject, wherein the catheter curves to conform to an inner surface of the cavity, and the course and/or position of the catheter within the cavity are determined using sensors fixed to the catheter.

It is a further object of the present invention to provide a method of determining the course of the catheter within the body.

In one aspect of the present invention, the course of the catheter may be determined within body cavities, in which the catheter is free to move in three dimensions, and not only within constraining lumens as in the prior art.

It is another object of the present invention, to provide catheters for insertion into a chamber of the subject's heart, for purposes of diagnostic mapping and/or therapeutic treatment in the interior of the chamber, along with methods for determining the course of the distal end of the catheter inside the heart chamber.

It is still a further object of the present invention to provide a method of therapeutic treatment of the heart using the catheter.

In preferred embodiments of the present invention, a flexible catheter, having a distal end for insertion into a cavity within the body of a subject, comprises first and second position sensors, fixed in a known relation to one another and to the distal end. The position sensors generates signals responsive to position coordinates thereof. The position-responsive signals are processed jointly to determine the positions of a plurality of points along the length of the catheter, inside the subject's body.

Most preferably, at least one of the position sensors comprises a plurality of magnetic-field-responsive coils, as described in the above-mentioned PCT publication WO96/05768, which enables six-dimensional position and orientation coordinates of the sensor to be determined. The other of the position sensors preferably comprises a similar plurality of coils, or, alternatively, it may comprise a single coil, as described in the above-mentioned U.S. Pat. No. 5,391,199. Further alternatively, any suitable position sensors known in the art may be used, such as electrical, magnetic or acoustic sensors, as long as the three-dimensional position coordinates of both the sensors and the three-dimensional orientation coordinates of at least one of the sensors can be determined from the sensor signals. The coordinates of the first and second sensors are determined and taken together with other, known information pertaining to curvature of the catheter intermediate the first and second sensors, as will be described below, to find the positions of a plurality of points along the length of the catheter in a vicinity of the first and second sensors.

In preferred embodiments of the present invention, the catheter is fed forward into a cavity of the body, for example, a chamber of the heart, the portion of the catheter intermediate the first and second position sensors is pressed against an inner wall of the cavity. Preferably, the catheter includes, along its length, one or more contact sensors, for example, pressure or proximity sensors, as are known in the art, for verifying that the catheter is in contact with or in sufficiently close proximity to the wall. The known coordinates of the first and second position sensors are then taken together with known features of the internal topography of the cavity to determine the curvature of the catheter and the positions of the plurality of points therealong. The topographical features may be known, for example, based on a previously- or simultaneously-acquired ultrasound or X-ray image, or determined using other methods known in the art. Preferably, the catheter is constructed so as to exert a generally uniform force per unit length against the inner wall of the cavity, so that in determining the curvature of the catheter, deformation of the wall is assumed to be minimized.

In some preferred embodiments of the present invention, the catheter includes one or more bend sensors, which generates signals responsive to a bend radius of the catheter in a vicinity thereof, and which signals are processed to determine a radius of curvature of the catheter. These embodiments are described in U.S. Provisional Patent Application Ser. No. 60/034,703, which is assigned to the assignee of the present patent application, and whose disclosure is incorporated herein by reference. The radius of curvature thus determined is used in finding the positions of the plurality of points along the catheter.

In some preferred embodiments of the present invention, the catheter includes physiological sensors, for example, electrophysiological sensing electrodes, spaced along its length. These sensors are preferably used to generate a map of physiological activity as a function of position within the body cavity.

In further preferred embodiments of the present invention, the catheter includes therapeutic devices at some or all of the plurality of points along its length. In one of these preferred embodiments, for example, the therapeutic devices comprise RF ablation electrodes, which are placed along a desired path against the endocardium by appropriately positioning the catheter, using the position and bend sensors, and are then activated to ablate heart tissue along this path. This method can be used in treating various conduction defects within the heart, including performing "maze procedures," as are known in the art, for alleviating atrial fibrillation.

Preferably, such therapeutic methods using the catheter are preceded by mapping the interior of the body cavity, such as the chamber of the heart, using either physiological sensors on the catheter, as described above, or imaging methods known in the art. The course of the catheter within the cavity, which is determined based on readings of the position and bend sensors, may then be registered with a map of the cavity, so as to ensure that the therapy is administered along the desired path.

In one such preferred embodiment, the RF ablation electrodes also serve as electrophysiological sensing electrodes when they are not being used for tissue ablation. The signals received from the electrodes are preferably analyzed and used to map electrical activity, described above, and/or to ascertain that the electrodes are suitably positioned, before performing the ablation.

While preferred embodiments of the present invention are generally described herein with reference to two position sensors, it will be appreciated that the inventive principles that they embody may be similarly applied to catheters, or to other probes, having a larger number of position sensors. Preferably, however, the number of such sensors is held to the minimum needed to acieve the desired accuracy of determination of the plurality of points along the length of the catheter, generally along the portion of the catheter adjacent the distal end thereof.

It will also be appreciated that although the preferred embodiments described herein make reference to catheters, and particularly to intracardiac catheters, it will be appreciated that the principles of the present invention may similarly be applied to other types of flexible medical probes, such as endoscopes.

There is therefore provided, in accordance with a preferred embodiment of the present invention, invasive probe apparatus including:

a flexible, elongate probe, having a distal end for insertion into the body of a subject, and including:
first and second position sensors, fixed in a known relation to the distal end, which generate signals responsive to position coordinates thereof; and
at least one contact sensor along a radial surface thereof, which generates signals responsive to contact of the radial surface with a surface inside the body; and
signal processing circuitry, which receives the position-responsive and contact-responsive signals and processes them to determine the locations of a plurality of points along the length of a portion of the probe in a vicinity of the first and second position sensors.

There is further provided, in accordance with another preferred embodiment of the present invention, a method for determining the course of an elongate, flexible probe inside the body of a subject, including:

bringing the probe into contact with a surface inside the body having known topographical features, along a portion of the length of the probe;

finding position coordinates of first and second points on the portion; and registering the course of the portion with the features, using the position coordinates of the first and second points.

There is additionally provided, in accordance with a preferred embodiment of the present invention, a method for mapping electrical activity in the heart of a subject, including:

inserting an elongate, flexible probe into the heart;

determining the course of the probe inside the heart, according to the method described above; and receiving electrical signals from heart tissue adjacent to the probe.

Moreover, in accordance with still another preferred embodiment of the present invention, there is provided a method for invasive therapeutic treatment of the heart of a subject, including:

inserting an elongate, flexible probe into the heart;

determining the course of the probe inside the heart, according to the method described above; and ablating heart tissue adjacent to the probe.

The present invention will be more fully understood from the following detailed description of the preferred embodiments thereof, taken together with the drawings in which:

DETAILED DESCRIPTION OF PREFERRED EMBODIMENTS

Figure 1:
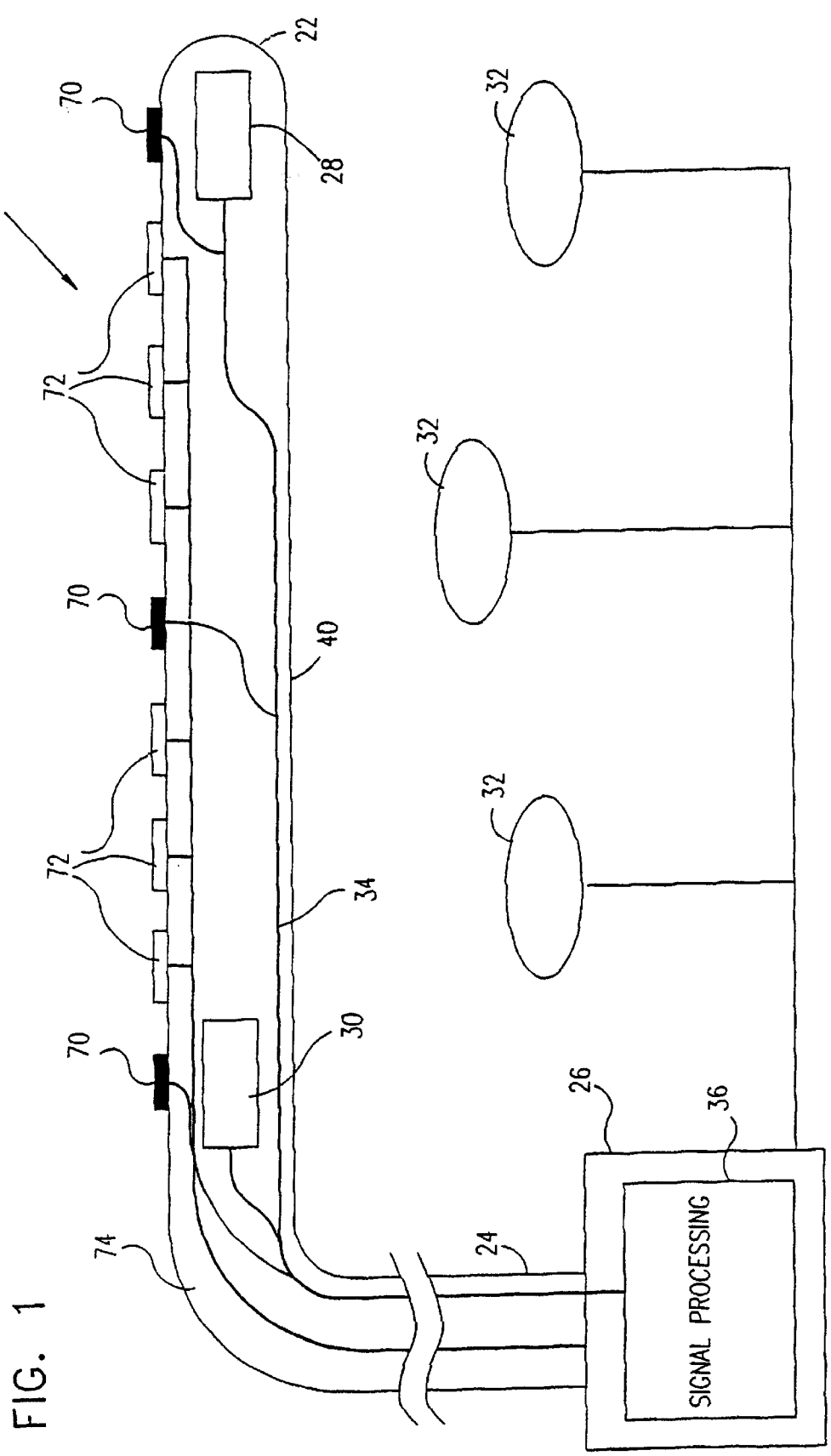
FIG. 1 is a schematic illustration of a conformal catheter system, in accordance with a preferred embodiment of the present invention.

Reference is now made to FIG. 1, which schematically illustrates a conformal catheter 20, in accordance with a preferred embodiment of the present invention, inserted into the heart of a subject, and a proximal end 24, which is coupled to a control console 26.

Adjacent to distal end 22, catheter 20 includes a first position-sensing element 28 and, proximal thereto, a second position-sensing element 30. Elements 28 and 30 define a generally distal portion 40 of catheter 20 therebetween. Preferably, each of elements 28 and 30 comprises three substantially orthogonal, non-concentric coils, as described in PCT publication WO96/05768, which generate signals responsive to magnetic fields applied by field generators 32. These signals are conveyed via wires 34 to signal processing and computing circuitry 36 in console 26, which preferably also provides driver and control signals to generators 32. Circuitry 36 analyzes the signals, as further described in the PCT publication, in order to determine the six-dimensional translational and orientational coordinates of elements 28 and 30 in relation to a frame of reference established by generators 32.

Figure 2:
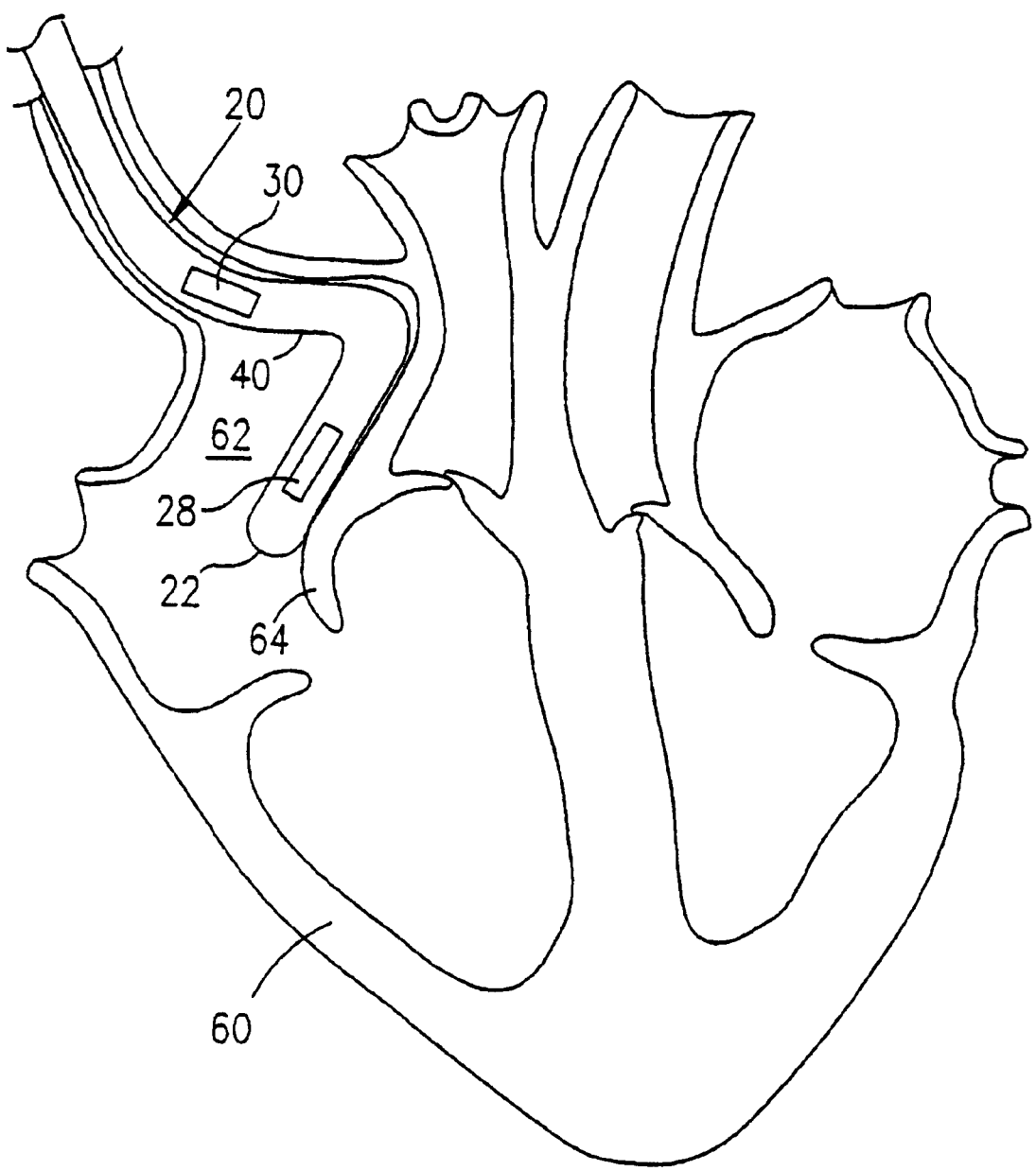
FIG. 2 is a schematic, partly sectional illustration showing the catheter of FIG. 1 inserted into a human heart, in accordance with a preferred embodiment of the present invention.

FIG. 2 schematically illustrates the insertion of catheter 20 into right atrium 62 of a human heart 60, in accordance with a preferred embodiment of the present invention. The curvature of portion 40 of catheter 20 is determined substantially by the curvature of an inner wall 64 of atrium 62 against which the catheter is brought to bear, in response to axial force exerted from the proximal end of the catheter.

The shape of inner wall 64 and a desired course of portion 40 against the wall are preferably known in advance of inserting catheter 20 into atrium 62. The shape and desired course may be derived from images of heart 60 acquired by any means known in the art, such as ultrasound, X-ray, or other imaging modality. Alternatively, the shape and desired course may be found by mapping the interior of heart 60, as described in the above-mentioned PCT patent application PCT/IL97/00009 or in U.S. patent application Ser. No. 08/476,200, filed Jun. 7, 1995, now U.S. Pat. No. 5,718,241, which are assigned to the assignee of the present invention, and whose disclosures are incorporated herein by reference, or by other mapping methods known in the art. Three-dimensional position coordinates of elements 28 and 30 and three dimensional orientation coordinates of at least one of the elements are determined and are referred to the known shape, in order to ascertain that portion 40 of catheter 20 is arrayed along the desired course in contact with wall 64. Preferably, portion 40 is sufficiently and homogeneously flexible, so as to exert a uniform force per unit length against wall 64. Thus, in determining the curvature of the portion, deformation of the wall is assumed to be minimized.

Referring again to FIG. 1, catheter 20 preferably includes optional pressure sensors 70 and ablation electrodes 72 (which are omitted in FIG. 2 for clarity). The output signals of pressure sensors 70 are coupled via wires 34 to signal processing circuitry 36, which analyzes the signals to determine whether catheter 20 is in contact along the length of portion 40 with wall 64. If the output signals of all of sensors 70 indicate that the sensors are at roughly equal respective positive pressures, due to force exerted between portion 40 and wall 64, it can then be assumed that portion 40 is conforming to the shape of the wall, which has been previously determined as described above. Proximity sensors or other sensors known in the art may be used in place of pressure sensors 70. It will be understood that there may be a greater or lesser number of pressure sensors or other sensors on catheter 20 than the three sensors 70 shown in FIG. 1, or no such sensors at all.

Ablation electrodes 72 receive RF energy, under the control of a physician or other user of catheter 20, from console 26 via wires 74, so as to ablate a row of desired sites that are adjacent to the electrodes on wall 64. Catheter 20 may include more or fewer ablation electrodes 72 than the six electrodes shown in FIG. 1, or no ablation electrodes. Other ablation devices, known in the art, may also be used.

Pressure sensors 70 and ablation electrodes 72 on catheter 20 are useful in performing certain therapeutic procedures. For example, catheter 20 as shown in FIGS. 1 and 2 may be used to perform a "maze" procedure, known in the art for treatment of atrial fibrillation (AF). In accordance with the present invention, the physician determines a linear or non-linear course along atrial wall 64 that should be ablated in order to interrupt abnormal conduction paths in the heart tissue that cause AF. Catheter 20 is inserted into heart 60 and portion 40 thereof is positioned along this course, in contact with wall 64, as described above. Electrodes 72 are then activated to ablate the entire course simultaneously, with greater speed and accuracy than are afforded by present methods of performing the maze procedure. Multiple courses may desirably be determined, and portion 40 of catheter 20 may be re-positioned and operated to ablate each of the courses in succession.

In other preferred embodiments of the present invention, sensing electrodes may be used in place of ablation electrodes 72, in order to map electrical activity within the heart tissue. A map of the interior of heart 60 that is generated using this method may then serve to guide therapeutic procedures, such as the "maze" procedure described above.

More generally speaking, while the preferred embodiments of the present invention have been described herein with reference to two position-sensing elements 28 and 30, it will be appreciated that for some applications, catheter 20 may preferably comprise a greater number of position sensors and/or of bend sensors. Such additional sensors may be particularly useful when a portion of the length of the catheter must be tracked within a convoluted passage, or when the catheter is brought to bear against and is desired to conform to a convoluted surface within a body cavity. Preferably, however, the number of such sensors is held to the minimum needed to achieve the desired accuracy of determination of the plurality of points along the length of the catheter.

Furthermore, in other preferred embodiments of the present invention, other devices and methods may be used to determine the curvature of portion 40 of catheter 20, for example, as described in the above-mentioned U.S. provisional patent application Ser. No. 60/034,703 and incorporated herein by reference.

It will be appreciated that although the preferred embodiments described above make reference to intracardiac catheter 20, the principles of the present invention may similarly be applied to other types of catheters, as well as other flexible medical probes, such as endoscopes.

It will also be appreciated that the preferred embodiments described above are cited by way of example, and the full scope of the invention is limited only by the claims.

What is claimed is:

1. Invasive probe apparatus comprising:
   a flexible, elongate probe, having a distal end for insertion into the body of a subject, comprising:
   first and second position sensors, fixed in a known relation to the distal end, which generate signals responsive to position coordinates thereof; and
   at least one contact sensor along a radial surface thereof, which generates signals responsive to contact of the radial surface with a surface inside the body; and
   signal processing circuitry, which receives the position-responsive and contact-responsive signals and processes them to determine the locations of a plurality of points along the length of a portion of the probe in a vicinity of the first and second position sensors.

2. Apparatus according to claim 1, wherein at least one of the position sensor comprises at least one coil, which generates signals responsive to an externally-applied magnetic field.

3. Apparatus according to claim 1, wherein the signal processing circuitry determines six-dimensional position and orientation coordinates of at least one of the position sensor.

4. Apparatus according to claim 1, and comprising a bend sensor.

5. Apparatus according to claim 1, wherein the at least one contact sensor comprises a pressure sensor.

6. Apparatus according to claim 1, wherein the at least one contact sensor comprises a proximity sensor.

7. Apparatus according to claim 6, and comprising a physiological sensor disposed along the length of the portion of the probe.

8. Apparatus according to claim 1 and comprising an ablation device disposed along the length of the portion of the probe.

9. Apparatus according to claim 8, wherein the ablation device comprises at least one RF electrode, radially disposed along the length of the portion.

10. Apparatus according to claim 9, wherein the at least one RF electrode comprises a longitudinal row of electrodes.

* * * * *